(12) United States Patent
Patel

(10) Patent No.: US 10,248,763 B2
(45) Date of Patent: Apr. 2, 2019

(54) HEALTHCARE PRESCRIPTION DELIVERY TECHNIQUES USING A MONEY TRANSFER NETWORK

(71) Applicant: Moneygram International, Inc., Minneapolis, MN (US)

(72) Inventor: Bhavesh Patel, London (GB)

(73) Assignee: Moneygram International, Inc., Minneapolis, MN (US)

( * ) Notice: Subject to any disclaimer, the term of this patent is extended or adjusted under 35 U.S.C. 154(b) by 548 days.

(21) Appl. No.: 14/869,739

(22) Filed: Sep. 29, 2015

(65) Prior Publication Data
US 2017/0091414 A1    Mar. 30, 2017

(51) Int. Cl.
G06F 19/00 (2018.01)
G06Q 10/08 (2012.01)
G16H 20/10 (2018.01)

(52) U.S. Cl.
CPC ........ G06F 19/3456 (2013.01); G06F 19/328 (2013.01); G06Q 10/08 (2013.01); G16H 20/10 (2018.01)

(58) Field of Classification Search
None
See application file for complete search history.

(56) References Cited

U.S. PATENT DOCUMENTS

| 2004/0019794 A1* | 1/2004 | Moradi | G06F 19/3462 713/185 |
| 2006/0006224 A1 | 1/2006 | Modi | |
| 2008/0306761 A1 | 12/2008 | George et al. | |
| 2011/0231283 A1* | 9/2011 | Li | G06O 20/02 705/26.41 |
| 2013/0103580 A1 | 4/2013 | Ventura | |
| 2014/0188643 A1* | 7/2014 | Murphy | G06Q 20/202 705/21 |
| 2014/0365237 A1* | 12/2014 | Oteng-Attakora | G06Q 90/00 705/2 |

OTHER PUBLICATIONS

International Search Report and Written Opinion issued for PCT Application No. PCT/US2016/42222, dated Sep. 29, 2016, 7 pages.
The extended European Search Report issued for European Patent Application No. 16852234.0, dated Aug. 16, 2018, 11 pages.
Isaac; Jesus; "Secure Mobile Payment Systems" published by IEEE Computer Society; Los Alamitos, CA, US; vol. 16; No. 3, 2014; pp. 36-43.

* cited by examiner

*Primary Examiner* — Valerie Lubin
(74) *Attorney, Agent, or Firm* — Norton Rose Fulbright US LLP

(57) ABSTRACT

A healthcare prescription delivery mechanism using a money transfer network is disclosed. In the healthcare prescription delivery mechanism, a prescription for a patient from a healthcare provider is sent to a designated pharmacy. The pharmacy then processes the prescription and delivers the prescribed medicine to a chosen address of the patient. A payment for the healthcare prescription order is made by either the patient or a third party through the money transfer network to the pharmacy.

15 Claims, 3 Drawing Sheets

HEALTHCARE PRESCRIPTION DELIVERY TECHNIQUES USING A MONEY TRANSFER NETWORK

TECHNICAL FIELD

The present disclosure relates to techniques for healthcare prescription delivery. In particular, the present disclosure relates to methods, apparatuses, and computer-readable storage media that provide techniques for delivering healthcare prescriptions to a patient or a third party via a money transfer network.

BACKGROUND

When a patient receives a healthcare prescription from a doctor, the patient or a third party, such as a family member, usually needs to travel to a pharmacy to fill the prescription and pay for it. In some situations, this can impose difficulties for the patient to receive the prescribed drug(s). For example, the patient may need a third party, such as his/her family member(s) to pay for the prescription. When the third party is located in a different place (e.g., a different city, state, and/or country) from the patient, the third party may be required to transfer the money to the patient through a financial institution (e.g., a bank or money transfer service provider), and the patient pays for the prescription at a pharmacy after receiving the funds. In some cases, the patient's illness or injury may prevent him/her from traveling to a pharmacy to fill the prescription and pay for it.

BRIEF SUMMARY

The present disclosure is directed to an integrated system and mechanism with a money transfer network and prescription drug delivery method that may allow a patient and/or a designated party to easily pay for a healthcare prescription and have the prescription delivered to a designated location for the patient. Embodiments of the present disclosure provide a healthcare prescription delivery mechanism that facilitates distribution of a prescription order using resources of a money transfer network. In an embodiment, the healthcare prescription delivery mechanism may include receiving a healthcare prescription order for a patient at a device of a money transfer network, sending, by the device, a notification to the patient or a third party regarding the healthcare prescription order, receiving a payment from the patient or the third party for the healthcare prescription order through the money transfer network, and sending, by the device, a message for preparing and delivering the prescription to a pharmacy chosen by the patient or the third party.

In an embodiment, the prescription delivery mechanism allows a third party located in a different location from the patient to conveniently pay for the patient's prescription order using the money transfer network. In an embodiment, the payment made by the patient or third party may be in a different currency than a currency used by the pharmacy that is processing and/or filling the healthcare prescription order. In such cases, the money transfer network may convert the payment made in the different currency into an amount in the currency used by the pharmacy before sending the payment to the pharmacy.

The foregoing has outlined rather broadly the features and technical advantages of the present disclosure in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the scope of the present disclosure as set forth in the appended claims. The novel features which are believed to be characteristic of embodiments described herein, both as to its organization and method of operation, together with further objects and advantages will be better understood from the following written description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

Figure 1:
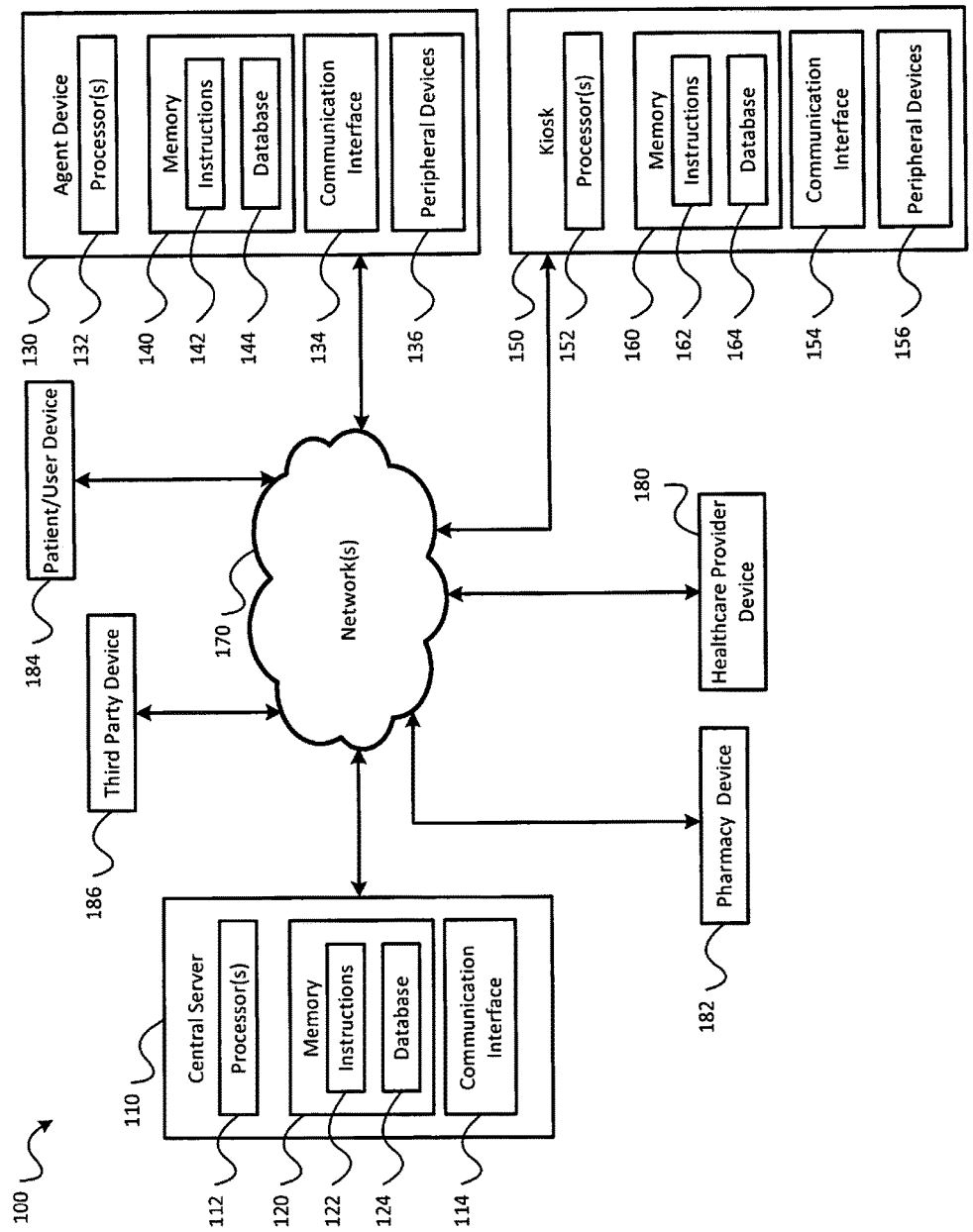
FIG. 1 is a block diagram of a system for healthcare prescription delivery using a money transfer network in accordance with aspects of the present disclosure.

Referring to FIG. 1, a block diagram of a system for healthcare prescription delivery using a money transfer network in accordance with aspects of the present disclosure is shown as a system 100. As shown in FIG. 1, the system 100 includes a central server 110, an agent device 130, a kiosk 150, a healthcare provider device 180, a pharmacy device 182, a patient/user device 184, and a third party device 186, each of which is communicatively coupled via network 170. It should be understood that in some cases, system 100 may not include all of the devices listed above. Rather, system 100 may comprise any combination of the devices described herein. The central server 110, the agent device 130, and the kiosk 150 may be operated by a money transfer service provider, and may be part of a money transfer network that includes other agent devices, kiosks, and servers that are geographically distributed (e.g., located in different parts of a city, located in different cities, located in different states, located in different countries, etc.).

As shown in FIG. 1, the central server 110 includes a processor 112, a communication interface 114, and a memory 120. It is noted that the processor 112 may include more than one processor, and each of the one or more processors may include one or more processor cores. The communication interface 114 may communicatively couple the central server 110 to the network 170, and may be configured to operate in accordance with one or more communication protocols (e.g., an institute of electrical and electronics engineers (IEEE) 802.11, 802.15, 802.16 communication standard, a cellular communication standard, or other wired and/or wireless communication standards and protocols).

The memory 120 may store instructions 122 and a database 124. The instructions 122 may include instructions that, when executed by the processor 112, cause the processor 112 to perform operations for processing prescription orders via a money transfer network, as described in connection with the central server 110 with reference to FIGS. 1-3. The database 124 may store information associated with one or more money transfer transactions provided money transfer locations operated by the money transfer service provider. For example, the database 124 may store profile information associated with one or more persons that have sent and/or received funds in connection with money transfer transactions provided by a money transfer location operated by the money transfer service provider, and may store transaction information associated with one or more money transfer transactions provided by money transfer locations operated by the money transfer service provider. The transaction information may include, for each money transfer transaction, information indicating a sending party (e.g., a party sending funds in connection with a money transfer transaction), a receiving party (e.g., a party receiving funds in connection with a money transfer transaction), an amount of funds transferred, a date the money transfer transaction was initiated, destination information indicating a money transfer location where the receiving party received the funds in connection with the money transfer transaction, origination information indicating a money transfer location where the sending party provided funds in connection with the money transfer transaction, other information, or a combination thereof. Additionally, the database 124 may store location risk information identifying locations known to be associated with fraudulent transactions, criminal activity, or other unscrupulous behaviors, which may be used to determine whether a prescription delivery transaction is associated with a location that is identified by the location risk information, as described in more detail below.

Further, database 124 may store information about one or more patients who have used, or are using healthcare prescription delivery technology or products through the money transfer network. For example, the database 124 may store information about one or more prescriptions received for a patient. The information about a prescription may include a name of a drug, a dose of the drug, an instruction on how to take the drug, personal information about the patient (such as age, gender, weight, height, race, diagnosis of a disease, and/or personal/family disease history), and/or an address where the prescribed drug(s) should be delivered to. Database 124 may also include information about payment for a prescription order for one or more patients. Such information may include information identifying one or more parties who are authorized by the patient to pay for the healthcare prescription order. The one or more authorized parties may include the patient or a third party willing to pay for the healthcare prescription order, such as a family member of the patient or a donor. The information about payment for the healthcare prescription order may also include contact information indicating how the patient and/or authorized third parties may be notified for making the payment for the healthcare prescription order, or whether the healthcare prescription order has been paid. The information about payment for the healthcare prescription order may include information indicating a currency preference for each of the parties that is authorized to pay for the healthcare prescription order. The currency preference information may be used by the money transfer network to determine whether the paying party is providing payment in a foreign currency (e.g., a currency that is different from a currency accepted by the pharmacy where the healthcare prescription order is to be processed) or a local currency (e.g., a currency that is the same as the currency accepted by the pharmacy where the healthcare prescription order is to be processed). Additionally, the database 124 may include information associated with conversion rates between various currencies.

In an embodiment, the database 124 may be located external to the central server 110. For example, the database 124 may be stored at a network attached storage device external to the central server 110, a remote server (not shown in FIG. 1), or another location that is accessible to the central server 110 via the network 170. It is noted that although a single central server 110 is shown in FIG. 1, the system 100 may include a plurality of central servers distributed across one or more regions where a money transfer service provider operates one or more money transfer locations.

As shown in FIG. 1, the agent device 130 includes a processor 132, a communication interface 134, and a memory 140. It is noted that the processor 132 may include more than one processor, and each of the one or more processors may include one or more processor cores. The communication interface 134 may communicatively couple the agent device 130 to the network 170, and may be configured to operate in accordance with one or more communication protocols (e.g., an IEEE 802.11, 802.15, 802.16 communication standard, a cellular communication standard, or other wired and/or wireless communication standards and protocols). The peripheral devices 136 may include a money order printer, an identification capture device (e.g., a signature pad, a camera, a pin pad module, a financial card reader, a biometric scanner, etc.), a receipt printer, another printing device, a barcode scanner, a metering device, a weight sensor, a check reader, a biometric input device (e.g., a fingerprint scanner, a retinal scanner, a palm print scanner, etc.), a microphone for receiving speech input, a keyboard, a mouse, other input devices, or any combination thereof. It is noted that although a single agent device 130 is shown in FIG. 1, the system 100 may include a plurality of agent devices distributed across one or more money transfer locations operated by a money transfer service provider.

The memory 140 may store instructions 142 and a database 144. The instructions 142 may include instructions that, when executed by the processor 132, cause the processor 132 to perform operations for processing prescription orders via a money transfer network, as described in connection with the agent device 130 with reference to FIGS. 1-3. The database 144 may store information associated with one or more money transfer transactions provided by a money transfer location (e.g., a money transfer location associated with the agent device 130) operated by the money transfer service provider. For example, the database 144 may store profile information associated with one or more persons that have sent and/or received funds in connection with money transfer transactions provided by a money transfer location where the agent device 130 is located, and may store transaction information associated with one or more money transfer transactions provided by the money transfer location where the agent device 130 is located. The transaction information may include, for each money transfer transaction, information indicating a sending party (e.g., a party sending funds in connection with a money transfer transaction), a receiving party (e.g., a party receiving funds in connection with a money transfer transaction), an amount of funds transferred, a date the money transfer transaction was initiated, destination information indicating a money transfer location where the receiving party received the funds in connection with the money transfer transaction, origination information indicating a money transfer location where the sending party provided funds in connection with the money transfer transaction, other information, or a combination thereof. Additionally, the database 144 may store location risk information identifying locations known to be associated with fraudulent transactions, criminal activity, or other unscrupulous behaviors, which may be used to determine whether a prescription delivery transaction is associated with a location that is identified by the location risk information, as described in more detail below.

Further, database 144 may store information about one or more patients who have used, or are using healthcare prescription delivery technology or products through the money transfer network. For example, database 144 may store information about one or more prescriptions received for a patient. The information about a prescription may include a name of a drug, a dose of the drug, an instruction on how to take the drug, personal information about the patient (such as age, gender, weight, height, race, diagnosis of a disease, and/or personal/family disease history), and/or an address where the prescribed drug(s) should be delivered to. Database 144 may also include information about payment for a prescription order for one or more patients. Such information may include information identifying one or more parties who are authorized by the patient to pay for the healthcare prescription order. The one or more authorized parties may include the patient or a third party willing to pay for the healthcare prescription order, such as a family member of the patient or a donor. The information about payment for the healthcare prescription order may also include contact information indicating how the patient and/or authorized third parties may be notified for making the payment for the prescription, or whether the healthcare prescription order has been paid. The information about payment for the healthcare prescription order may also include information indicating a currency preference for each of the parties that is authorized to pay for the healthcare prescription order. The currency preference information may be used by the money transfer network to determine whether the paying party is providing payment in a foreign currency (e.g., a currency that is different from a currency accepted by the pharmacy where the healthcare prescription order is to be processed) or a local currency (e.g., a currency that is the same as the currency accepted by the pharmacy where the healthcare prescription order is to be processed). Additionally, the database 144 may include information associated with conversion rates between various currencies.

In an embodiment, the database 144 may be located external to the agent device 130. For example, the database 144 may be stored at a network attached storage device external to the agent device 130, a server (not shown in FIG. 1) remote to, or local to a money transfer location where the agent device 130 is located, or another location that is accessible to the agent device 130 via the network 170.

As shown in FIG. 1, the kiosk 150 includes a processor 152, a communication interface 154, and a memory 160. It is noted that the processor 152 may include more than one processor, and each of the one or more processors may include one or more processor cores. The communication interface 154 may communicatively couple the kiosk 150 to the network 170, and may be configured to operate in accordance with one or more communication protocols (e.g., an IEEE 802.11, 802.15, 802.16 communication standard, a cellular communication standard, or other wired and/or wireless communication standards and protocols). The peripheral devices 156 may include a money order printer, an identification capture device (e.g., a signature pad, a camera, a pin pad module, a financial card reader, a biometric scanner, etc.), a receipt printer, another printing device, a barcode scanner, a metering device, a weight sensor, a check reader, a biometric input device (e.g., a fingerprint scanner, a retinal scanner, a palm print scanner, etc.), a microphone for receiving speech input, a keyboard, a mouse, other input devices, or any combination thereof. It is noted that although a single kiosk 150 is shown in FIG. 1, the system 100 may include a plurality of kiosks distributed across one or more locations, which may include money transfer locations operated by a money transfer service provider, and may include other locations operated by entities other than the money transfer service provider, such as at grocery stores, malls, or other locations.

The memory 160 may store instructions 162 and a database 164. The instructions 162 may include instructions that, when executed by the processor 152, cause the processor 152 to perform operations for healthcare prescription delivery via a money transfer network, as described in connection with the kiosk 150 with reference to FIGS. 1-3. The database 164 may store information associated with one or more money transfer transactions provided by a money transfer location (e.g., a money transfer location associated with the kiosk 150) operated by the money transfer service provider. For example, the database 164 may store profile information associated with one or more persons that have sent and/or received funds in connection with money transfer transactions provided by a money transfer location where the kiosk 150 is located, and may store transaction information associated with one or more money transfer transactions provided by the money transfer location where the kiosk 150 is located. The transaction information may include, for each money transfer transaction, information indicating a sending party (e.g., a party sending funds in connection with a money transfer transaction), a receiving party (e.g., a party receiving funds in connection with a money transfer transaction), an amount of funds transferred, a date the money transfer transaction was initiated, destination information indicating a money transfer location where the receiving party received the funds in connection with the money transfer transaction, origination information indication a money transfer location where the sending party provided funds in connection with the money transfer transaction, other information, or a combination thereof. Additionally, the database 164 may store location risk information identifying locations known to be associated with fraudulent transactions, criminal activity, or other unscrupulous behaviors, which may be used to determine whether a prescription delivery transaction is associated with a location that is identified by the location risk information, as described in more detail below.

Further, database 164 may store information about one or more patients who have used or is using healthcare prescription delivery through a money transfer network. For example, database 164 may store information about one or more prescriptions received for a patient. The information about a prescription may include a name of a drug, a dose of the drug, an instruction on how to take the drug, personal information about the patient (such as age, gender, weight, height, race, diagnosis of a disease, and/or personal/family disease history), and/or an address where the prescribed drug(s) should be delivered to. Database 164 may also include information about payment for a prescription order for one or more patients. Such information may include information identifying one or more parties who are authorized by the patient to pay for the healthcare prescription order. The one or more authorized parties may include the patient or a third party willing to pay for the healthcare prescription order, such as a family member of the patient or a donor. The information about payment for the healthcare prescription order may also include contact information indicating how the patient and/or authorized third parties may be notified for making the payment for the healthcare prescription order, or whether the healthcare prescription order has been paid. The information about payment for the healthcare prescription order may also include information indicating a currency preference for each of the parties that is authorized to pay for the healthcare prescription order. The currency preference information may be used by the money transfer network to determine whether the paying party is providing payment in a foreign currency (e.g., a currency that is different from a currency accepted by the pharmacy where the healthcare prescription order is to be processed) or a local currency (e.g., a currency that is the same as the currency accepted by the pharmacy where the healthcare prescription order is to be processed). Additionally, the database 164 may include information associated with conversion rates between various currencies.

In an embodiment, the database 164 may be located external to the kiosk 150. For example, the database 164 may be stored at a network attached storage device external to the kiosk 150, a server (not shown in FIG. 1) remote to, or local to a money transfer location where the kiosk 150 is located, or another location that is accessible to the kiosk 150 via the network 170.

As shown in FIG. 1, the central server 110, the agent device 130, and the kiosk 150 may be communicatively coupled to the healthcare provider device 180, the pharmacy device 182, the patient/user device 184, and the third party device 186 via the network 170. In an embodiment, the network 170 may be a wired network, a wireless network, or may include a combination of wired and wireless networks. For example, the network 170 may be a local area network (LAN), a wide area network (WAN), a wireless WAN, a wireless LAN (WLAN), a metropolitan area network (MAN), a wireless MAN network, a cellular data network, a cellular voice network, a public network (e.g., the internet), a private network (e.g., a private money transfer network operated by a money transfer service provider), other types of networks, or a combination thereof. In an embodiment, the network 170 may include multiple networks operated by different entities. For example, the network 170 may include a first network (e.g., a private money transfer network) operated by the money transfer service provider to facilitate communication between the central server 110, the kiosk device 150, and a facilities where one or more agent device(s) 130 are located, and a second network (e.g., a public network) that facilitates communication between the healthcare provider device 180, the pharmacy device 182, the patient/user device 184, the third party device 186, and the money transfer service provider devices, such as the central server 110, the agent device 130, and/or the kiosk 150.

In an embodiment, the healthcare provider device 180 may be a server, a personal computer device, a tablet computing device, a mobile communication device, a smartphone device, a laptop computing device, another computing device, or a combination thereof, and may be operated by a healthcare provider that provides healthcare and/or a prescription services to individuals (e.g., an operator of the patient/user device 184). In an embodiment, the pharmacy device 182 may be a personal computer device, a tablet computing device, a mobile communication device, a smartphone device, a laptop computing device, another computing device, or a combination thereof that processes a prescription order for a patient (e.g., an operator of the patient/user device 184). In an embodiment, the patient/user device 184 may be a personal computer device, a tablet computing device, a mobile communication device, a smartphone device, a laptop computing device, another computing device, or a combination thereof.

In an embodiment, during operation, a healthcare prescription order may be received at a device (e.g., one of the central server 110, the agent device 130, or the kiosk 150) of a money transfer network. The healthcare prescription order may be generated by a healthcare provider (e.g., an operator of the healthcare provider device 180) in connection with a diagnosis of a patient's disease, illness, injury, etc. The healthcare prescription order may be generated in response to a physical visit to a healthcare provider facility by the patient, or from an online diagnosis by an online doctor based on symptoms, images, and/or other information provided by the patient. It should be noted that a doctor, as used herein, includes an individual with a medical degree or any other individuals (such as a registered nurse) who are authorized to provide a prescription orders and healthcare services to the patient.

In an embodiment, the healthcare prescription order may be received at the device (e.g., the central server 110, agent device 130, or the kiosk 150) of the money transfer network directly from a healthcare provider through the healthcare provider device 180. For example, the healthcare provider may use the healthcare provider device 180 to e-mail or fax the healthcare prescription order to the device of the money transfer network. Additionally or alternatively, an operator of the healthcare provider device 180 may navigate to a web page (or utilize functionality provided by an application programming interface (API)) provided by via the money transfer network, and may interact with the web page (or devices of the money transfer network) to fill out and submit a form to the device of the money transfer network, where the form includes the healthcare prescription order. Alternatively or additionally, the healthcare prescription order may be provided from a healthcare provider to the patient or third party (such as the patient's family member or another designated person). In this case, the healthcare prescription order may be received at the device of the money transfer network from the patient through the patient/user device 184, from the third party through the third party device 186, or via input to the kiosk 150 or the agent device 130. For example, the patient or third party may provide inputs associated with the healthcare prescription order to the kiosk 150 autonomously, or may be assisted by an agent of the money transfer service provider operating the kiosk 150. As another example, the healthcare prescription order may be received from the agent device 130 in connection with an interaction between the patient or third party and an agent operating the agent device 130. In an embodiment, the agent device 130 and/or the kiosk 150 may be configured to present one or more graphical user interfaces (GUIs) at a display device, where the one or more GUIs prompt the agent or patient/third party to provide inputs corresponding to the healthcare prescription order.

In an additional or alternative embodiment, a user of the pharmacy device 182 may submit the healthcare prescription order to the device of the money transfer network by filling out a form on a web page (e.g., the web page provided by the money transfer service provider), and the healthcare prescription order may be received at the device of the money transfer network in response to a submission of the form. Additionally or alternatively, the healthcare prescription order may be generated using an input device coupled to the pharmacy device 182, such as an imaging device (e.g., an image scanner, a camera, etc.) or an audio and/or video recorder, and the resulting image, audio and/or video indicating the healthcare prescription order may be sent to central server 110 or other device of the money transfer network.

In an additional or alternative embodiment, the healthcare prescription order may be received at the device of the money transfer network from the patient/user device 184. The healthcare prescription order may be generated by filling out and submitting a form on a web page, and the submitted form may be received by the central server 110. The healthcare prescription order may also be generated using an input received at the patient/user device 184, such as an imaging device (e.g., an image scanner, a camera, etc.) or an audio and/or video recorder, and the resulting image, audio and/or video indicating the healthcare prescription order may be sent to central server 110 or other device of the money transfer network.

In an embodiment, the healthcare prescription order may include a name of a drug, a dosage of the drug, a price of the drug, and/or a medical device prescribed for the patient. The healthcare prescription order may also include information of the patient, such as the patient's name, age, gender, birth date, weight, height, address, social security number, e-mail address, telephone number, place of employment, symptom, diagnosis, etc. The healthcare prescription order may also include information identifying a pharmacy chosen by the patient or third party, and/or an address where the prescribed drug(s) may be delivered to. In an embodiment, the patient and/or a third party may designate a pharmacy to the doctor before the doctor places the healthcare prescription order, and the healthcare prescription order may indicate the designated pharmacy. In an additional or alternative embodiment, the healthcare prescription order may not indicate the designated pharmacy. For example, the profile information (e.g., as stored at one or more of the database(s) 124, 144, 164) associated with the patient may include information indicating a preferred or designated pharmacy for the patient and/or third party. The designated pharmacy information may be used by the device of the money transfer network to determine which pharmacy the healthcare prescription order should be sent to so that the healthcare prescription order may be filled, or may be used by the device of the money transfer network to determine which pharmacy service should be used to validate the healthcare prescription order, as described in more detail below. In yet another additional or alternative embodiment, the patient and/or third party may designate the pharmacy where the healthcare prescription order is to be filled when making a payment for the healthcare prescription order.

In still another additional or alternative embodiment, the database (e.g., one or more of the databases 124, 144, 164) may store prescription order cost information that identifies costs for various prescription drugs at a plurality of pharmacy locations. Such information may be used to make a recommendation to the patient and/or third party regarding where the healthcare prescription order may be most cost effectively filled. In an embodiment, the pharmacy recommendations may be further based on insurance plan information associated with a health insurance plan of the patient and/or the third party (e.g., in the case where the patient is a minor or otherwise covered by the third party's health insurance plan). This cost information stored at the database(s) of the money transfer network may be obtained during processing of prescription order payments received via the money transfer network. Exemplary techniques for receiving payment for prescription orders via the money transfer network are described in more detail below.

In an embodiment, after the healthcare prescription order is received at the device of the money transfer network, the device may provide a notification to the patient and/or third party designated by the patient regarding the healthcare prescription order. In an embodiment, the notification may be provided to the patient and/or third party via an e-mail message, a text message, an automated voice response message, a voice call, or a combination thereof. The notification may provide the patient and/or third party with detailed information about the healthcare prescription, and/or directions about how/where/when to make a payment for the healthcare prescription order. In an embodiment, a unique identifier may be associated with the healthcare prescription order. In an embodiment, only the unique identifier is provided to the patient and/or third party in the notification, and the patient and/or third party may use the unique identifier to retrieve details of the healthcare prescription order by logging into a web page provided by the money transfer network (e.g., by the central server 110). Including only the unique identifier may reduce the risk that unauthorized third parties intercept the notification and learn that the notification is related to a healthcare prescription order that is to be filled. Further, even if the notification containing the unique identifier is intercepted by an unauthorized third party, such party would be unable to obtain details of the healthcare prescription order without also having knowledge of the patient's login information.

During operation, the healthcare prescription order information may be validated to verify that the healthcare prescription order is a valid healthcare prescription order that has not been filled. Additionally, validation of the healthcare prescription order may be performed for other purposes as well, such as to prevent people from obtaining prescription medications by means of fraud. It is noted that the validation of the healthcare prescription of the healthcare prescription order information may be performed for other purposes, and that the exemplary reasons for performing validation provided herein are provided for purposes of illustration, rather than by way of limitation.

In an embodiment, validating the healthcare prescription order may include establishing a communication connection between the central server 110 of the money transfer network and a server associated with a pharmacy service (e.g., an entity operating the pharmacy device 182), where the pharmacy service may correspond to the pharmacy (or a chain of pharmacies) identified for filling the healthcare prescription order, and the server may be a centrally located server serving a plurality of pharmacy locations, or a local server serving the particular location where the healthcare prescription order is to be filled. In an embodiment, the healthcare prescription order may be provided from a device at an agent location (e.g., the agent device 130 or the kiosk 150) to the central server 110, and the central server 110 may establish the communication connection in response to receiving the healthcare prescription order information from the device.

In an embodiment, validating the healthcare prescription order information may also include providing at least a portion of the received healthcare prescription order information to the server. For example, the portion of the received healthcare prescription order information may include the unique identifier associated with the healthcare prescription order information, the patient's name, a name and dose of the prescribed drug, a quantity of the prescribed drug that is to be provided to the patient in connection with the healthcare prescription order, other information, or a combination thereof. The server may verify that the portion of the received healthcare prescription order information matches the pharmacy service's records (e.g., information associated with the healthcare prescription order that has been received from the prescribing doctor, etc.). Upon verifying the portion of the received healthcare prescription order information, the server may provide a validation determination to the central server 110. The validation determination may indicate whether the healthcare prescription order is valid.

The central server 110 may receive the validation determination from the server of the pharmacy service, and may transmit the validation determination to device at the agent location. In response to receiving validation information that indicates the healthcare prescription order is valid, the device may initiate operations to facilitate payment for the healthcare prescription order. For example, in response to receiving validation information that indicates the healthcare prescription order is valid, the device may configure a money transfer transaction between a receiving party and a sending party, where the sending party corresponds to the patient or a third party, and the receiving party is associated with the pharmacy service that validated the healthcare prescription order. Additionally, the device may receive payment information associated with a payment for the healthcare prescription order. The payment may be used to fund the money transfer transaction so as to provide payment for the healthcare prescription order. In an embodiment, the payment may be provided by the patient or a third party at the agent location. In an additional or alternative embodiment, the patient or third party may provide the payment via a GUI presented via a web page provided by the operator of the money transfer network. Upon receiving payment for the healthcare prescription order, the device may initiate the money transfer transaction to provide payment for the healthcare prescription order. In an embodiment, the device may also transmit a notification to the pharmacy service that the payment has been received from the sending party. Upon providing the notification to the pharmacy service that the payment has been received, the patient or a designated third party may pick up the prescribed drugs from the pharmacy location designated by the patient.

It is noted that the validation of the healthcare prescription order information, and the operations to facilitate payment for the healthcare prescription order, although described as including actions performed by both the central server and the device, may be performed entirely by a single device. For example, when the healthcare prescription order information and payment information is provided to the money transfer network using a browser-based application or mobile application, the validation and operations to provide payment for the healthcare prescription order may be performed entirely by central server 110. As another example, when the healthcare prescription order information and payment information is provided to the money transfer network via the kiosk 150 and/or the agent device 130, the validation and operations to provide payment for the healthcare prescription order may be performed entirely by the kiosk 150 and/or the agent device 130. It is noted that other combinations of devices and operations may be performed by the various devices of the money transfer network to validate and provide payment for healthcare prescription orders, and exemplary combinations of devices and operations are provided above for purposes of illustrating how devices of a money transfer network may be utilized to facilitate healthcare prescription delivery, rather than by way of limitation.

During operation, a payment for the healthcare prescription order may be received at a device (e.g., one of the central server 110, the agent device 130, or the kiosk 150) of the money transfer network, as described above. In an embodiment, the payment may be received from the patient to whom the healthcare prescription order was provided. The patient may make the payment using the patient/user device 184 by entering his/her payment information at a web page provided by the money transfer network, such as through the central server 110, or via an application provided by the money transfer service provider that has been installed on the patient/user device 184. The payment information may include the patient's bank account information, financial card information (e.g., credit card, debit card, store value card, etc.), electronically depositing a check to an account associated with the money transfer service provider (e.g., via the application installed on the patient/user device 184 or via functionality provided via the web page), providing audio/video instructions about payment information, and/or any other information necessary for making a payment. Alternatively or additionally, the payment may be made by the patient using the kiosk 150 by entering the payment information using one or more GUIs provided by the kiosk 150. Alternatively, the payment may be made by the patient providing the payment information to the agent device 130 and/or kiosk 150 with the assistance of an agent of the money transfer service provider. In an embodiment, the patient may use the unique identifier to identify the healthcare prescription order when making the payment.

In an embodiment, the payment for the healthcare prescription order may be made by a third party. The third party may be a family member or relative of the patient or another party who is willing to pay for the healthcare prescription order for the patient. For example, the third party may be an individual or entity who wants to pay for the healthcare prescription order for good will, charity, or other beneficial societal purposes. The payment may be made by the third party using the third party device 186, the kiosk 150, or the agent device 130 (e.g., with the assistance of an agent operating the agent device 130) with the third party providing his/her payment information. In an embodiment, the third party who makes the payment for the healthcare prescription order may be located in a different place from the patient (e.g., the third party may be in a different area of a city, in a different city, or in a different country from the patient), as described further in connection with FIG. 3.

During operation, a pharmacy may be able to receive the healthcare prescription order and/or the payment of the healthcare prescription order from a device of the money transfer network via network 170, or using the pharmacy device 182 through the network 170. For example, in an embodiment, the devices of the money transfer network may operate as an intermediary between the healthcare service provider that generated the healthcare prescription order, the patient/third party, and the pharmacy, where the patient/third party sends the payment to the money transfer network, and then the money transfer network provides funds of the payment to the pharmacy. In some cases, the payment for the healthcare prescription order may be made in a currency that is different from the currency used by the pharmacy. For example, the payment may be made by a patient's family member in a first location (e.g., in China) in a first currency (e.g., in Chinese Yuan), while the pharmacy may be located in a second location (e.g., in the United States) and may use a second currency (e.g., U.S. dollar). In such cases, the system 100 may convert the payment received in the foreign currency into an amount in a local currency of the pharmacy based on a conversion rate using the money transfer network, or vice versa. In an embodiment, the currency used by the patient/third party to make the payment and/or the conversion rate may be stored in the profile of the patient/third party. Alternatively, the money transfer network can automatically detect that the payment is made in a different currency than the currency used by the pharmacy, and determine a conversion rate. For example, when a third party is paying for a prescription order of $100 US dollars and the money transfer network determines that the payee (the patient/third party) is paying in Japanese Yen, the money transfer network may convert the amount of the healthcare prescription order into Japanese Yen and display the amount in Japanese Yen to the payee.

The an embodiment, the money transfer network may detect that the payment is being received in a foreign currency based on a location of the device where the payment information is received. For example, in the scenario above, the third party may provide the unique identifier associated with the healthcare prescription order for which payment is to be made at a kiosk (e.g., the kiosk 150) located in Japan, and the system may determine that the unique identifier is associated with a prescription order that is to be filled at a pharmacy in the United States. Thus, the system may determine the amount of funds to be provided in U.S. dollars to pay for the healthcare prescription order, convert the amount of funds (in U.S. dollars) to an amount in the foreign currency (e.g., Japanese Yen), and then present the amount in the foreign currency to the paying party to inform the paying party of the amount to be paid. Presenting the payment amount in the currency for which payment is to be received may provide several advantages. For example, in some instances, there may not be an even conversion of the payment amount between different currencies, which means that sometimes the amount paid in a foreign currency may be a slightly higher or lower than the actual payment amount due. The presentation of the payment amount in the foreign currency may be configured to ensure that the paid amount is at least the same as, or slightly larger than, the actual payment amount due. This ensures that the pharmacy receives payment in full for the healthcare prescription order. In an embodiment, the money transfer network may add small fee to the actual payment amount due, and, if there is not an even conversion between different currencies, may reduce the fee to ensure an even conversion. For example, if the fee is $5.00 and the actual payment amount due is $100.00 U.S. dollars, but the conversion rate is such that the only even amounts in the foreign currency to pay the $105.00 are equivalent to $105.27 or $104.68, the money transfer network may reduce the $5.00 fee to $4.68 to ensure that the pharmacy receives payment in full while keeping the amount paid in the foreign currency to an exact amount due (i.e., the paying party is not owed any change by the money transfer network).

Resources of the money transfer network may be utilized to assist the patient and/or third party to make payment for the healthcare prescription order and/or to assist the pharmacy to receive the payment. The resources of the money transfer network that may be utilized include a database (e.g., the database 124, 144, and/or 164) of the money transfer network. As explained above, the database may store money transfer transaction information associated with money transfer transactions that were provided via the money transfer network. For example, in response to a payment request, the device (e.g., the central server 110, the agent device 130, or the kiosk 150) may determine whether money transfer transaction information stored by the database includes money transfer transaction information associated with the payer. If the payer's payment information (such as bank account number, routing number, etc.) is already stored in the database, the system may indicate to the payee that the stored information may be used for the current payment. Further, if the healthcare prescription order is to be filled at a location identified by the location risk information, the healthcare prescription order may be flagged, where flagging the healthcare prescription order may cause the pharmacy to implement enhanced procedures for authenticating the party picking up the healthcare prescription order.

In response to receiving an indication that the payment for the healthcare prescription order has been accepted or denied, the device may provide a notification to patient and/or third party who made the payment (e.g., to the patient and/or third party via the patient/user device 184, kiosk 150, or the agent device 130). In an embodiment, the notification may be provided to the patient/third party via an e-mail message, a text message, an automated voice response message, a voice call, or a combination thereof.

After the payment for the prescription has been accepted, system 100 may provide a notification to the pharmacy (e.g., through the pharmacy device 182) where the healthcare prescription order is to be filled, or a server associated with a pharmacy service, as described above. The notification may be provided to the pharmacy via an e-mail message, a text message, an automated voice response message, a voice call, or a combination thereof. The notification may indicate that the payment for the healthcare prescription order has been received, and the healthcare prescription order is ready to be filled. In an embodiment, the notification of payment may be indicated in the healthcare prescription order itself when the healthcare prescription order is sent to the pharmacy. For example, in an embodiment, the money transfer network may delay sending the healthcare prescription order until it has been paid for and/or validated. In some cases, the healthcare prescription order and the notification of payment may be separately sent to the pharmacy. For example, in an embodiment, the healthcare prescription order may be sent to the pharmacy before the payment has been made, which may reduce delays that occur when the patient or third party attempts to pick up the healthcare prescription order at the pharmacy.

Subsequent to receiving the healthcare prescription order and/or notification of payment for the healthcare prescription order, the pharmacy may fill the prescription. The filled prescription may either be: 1) delivered to an address designated by the patient; or 2) stored at the pharmacy for the patient and/or a third party to pick up. The pharmacy may provide a notification of the status of the healthcare prescription order (e.g., the payment has been received, the prescription is ready for delivery/pick up, the prescription has been delivered, etc.) to the patient and/or third party through network 170 (e.g., using pharmacy device 182). In an embodiment, the patient and/or third party may use the unique identifier associated with the healthcare prescription order to pick up the healthcare prescription order.

The unique identifier assigned to the healthcare prescription order may be used in many different ways. In an embodiment, the unique identifier may be used by system 100 to process the healthcare prescription order, receive a payment of the healthcare prescription order, create a status of the healthcare prescription order, make a notification regarding the healthcare prescription order to the patient/third party, or a designated pharmacy. The unique identifier may also be used by the patient and/or a third party to make a payment for and/or and inquiry about the status of the healthcare prescription order. The unique identifier may also be used by the pharmacy to process, deliver, or make a notification about the healthcare prescription order. The unique identifier may provide a convenient way to keep track of the healthcare prescription order throughout the prescription delivery process. For example, the money transfer network can use the unique identifier to keep track of whether a notification of the issuance of the healthcare prescription order has been sent to the patient and/or third party, whether a payment has been received, whether the healthcare prescription order has been sent to the pharmacy, whether the pharmacy has processed and delivered the prescription, etc. Similarly, the patient, third party, and/or the pharmacy can keep track of the healthcare prescription order throughout the process using the unique identifier (e.g., by logging into a web page provided by the money transfer network, or using an application on a mobile device, etc.).

Figure 2:
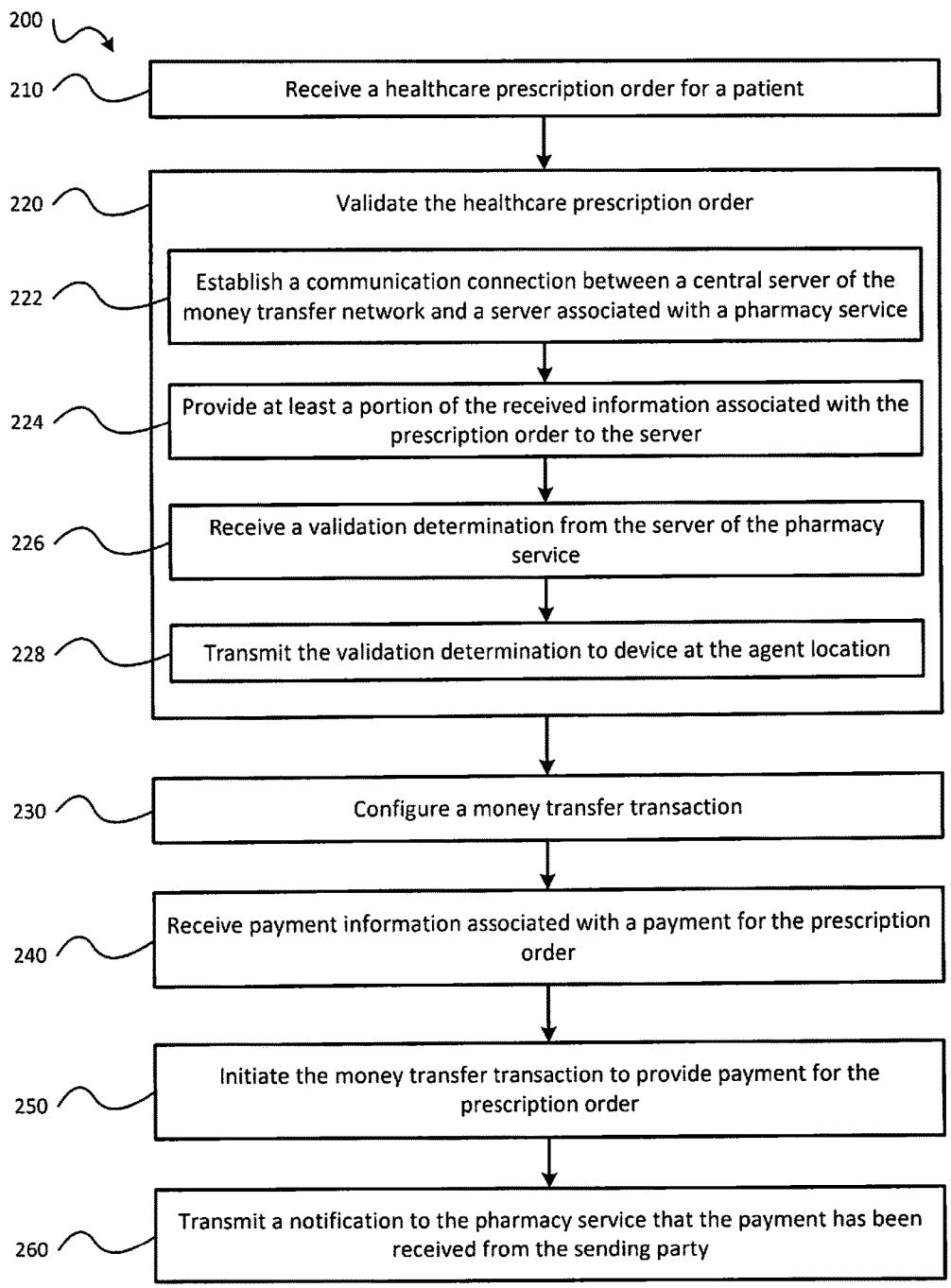
FIG. 2 is a flowchart illustrating aspects of a method for healthcare prescription delivery using a money transfer network in accordance with aspects of the present disclosure.

Referring to FIG. 2, a flow diagram illustrating an exemplary embodiment of a method for healthcare prescription delivery via a money transfer network in accordance with aspects of the present disclosure, shown as a method 200. In an embodiment, the method 200 may be stored as instructions (e.g., one or more of the instructions 122, 142, 162 of FIG. 1) that, when executed by a processor (e.g., one or more of the processors 112, 132, 152), cause the processor to perform operations for utilizing resources of a money transfer network to process a healthcare prescription delivery. In an embodiment, the method 200 may be performed by the central server 110 of FIG. 1, the agent device 130 of FIG. 1, the kiosk 150 of FIG. 1, or any combination thereof.

At 210, the method 200 includes receiving a healthcare prescription order for a patient using a device of a money transfer network. The device receiving the order may be one or more of the money transfer network devices described in FIG. 1, such as the agent device 130, the kiosk 150, and/or the central server 110. In an embodiment, the healthcare prescription order may include an unique identifier associated with the healthcare prescription order, an identification of the patient (e.g., name, birthday, social security number, driver's license number, etc.), a name of a drug, a dose of the drug, a medical device, and contact information of the patient (e.g., phone number, email address, mailing address, etc.), other healthcare prescription order information described above with respect to FIG. 1, or any combination thereof.

At 220, the method 200 includes validating the healthcare prescription order. In an embodiment, the validation may be performed as described with reference to FIG. 1. For example, the validating of the healthcare prescription order may include, at 222, establishing a communication connection between a central server of the money transfer network and a server associated with a pharmacy service, and, at 224 providing at least a portion of the received information associated with the healthcare prescription order to the server. At 226, the validation may include receiving a validation determination from the server of the pharmacy service. In an embodiment, the validation determination may indicate whether the healthcare prescription order is valid, as described with reference to FIG. 1. In embodiments where the validation is performed by the central server, the method 200 may include, at 228, transmitting the validation determination to device at the agent location. In an embodiment, the device may be the kiosk device 150 or the agent device 130 of FIG. 1.

At 230, the method 200 may include configuring a money transfer transaction in response to receiving validation information that indicates the healthcare prescription order is valid. In an embodiment, the money transfer transaction may be between a receiving party and a sending party, where the sending party may be the patient or a third party, and the receiving party may be associated with the pharmacy service that validated the healthcare prescription order. Additionally, at 240, the method 200 may include receiving payment information associated with a payment for the healthcare prescription order in response to receiving validation information that indicates the healthcare prescription order is valid. In an embodiment, the payment from the patient/third party may be received utilizing resources of the money transfer network. For example, the resources of the money transfer network may include a database (e.g., one or more of the databases 124, 144, 164 of FIG. 1) of the money transfer network. The database(s) may store money transfer transaction information associated with money transfer transactions provided via the money transfer network. The payment may be made by the patient, or by the third party, using one or more devices described in FIG. 1, such as the pharmacy device 182, patient/user device 184, third party device 186, agent device 130, kiosk 150, and/or central server 110. The payment may be made online by the patient or third party using any of these devices, or may be made in person at a location of the money transfer network with the assistance of an agent (e.g., an operator of the agent device 130 described in FIG. 1) using resources of the money transfer network. The payment may be used to fund the money transfer transaction. At 250, the method 200 includes initiating the money transfer transaction to provide payment for the healthcare prescription order, and, at 260, includes transmitting a notification to the pharmacy service that the payment has been received from the sending party.

In an embodiment, the method 200 may include additional operations. For example, the method 200 may include sending a notification to the patient and/or a third party regarding the healthcare prescription order. The third party may be a family member, a relative, or any other individual/entity designated by the patient. The third party may also be an individual/entity that is not designated by the patient but is willing to pay for the prescription (e.g., for charity purposes). For example, an individual/entity may be willing to pay for a prescription order for an indigent patient out of good will. This may be especially true for patients in some countries around the world. For example, individuals in poverty stricken parts of the world may need money to obtain prescription medicines for various diagnosed conditions, injuries, or illnesses, and individuals having the means to donate money to pay for such prescriptions may provide funds to the patients or pharmacies to pay for those prescriptions, allowing those persons to obtain the medical care that they need. The notification may inform the patient/third party that a prescription order has been placed for him/her, and may allow the pharmacy to find out details of the prescription on a database such as databases 124, 144, 164 described in FIG. 1. The notification may also provide more detailed information about the healthcare prescription order, such as name of the drug(s), dosage(s)/prices of the drug(s), and how/when to make a payment for the healthcare prescription order, etc. The notification may be provided to the patient and/or third party via an e-mail message, a text message, an automated voice response message, a voice call, or a combination thereof. The notification may also provide the patient and/or third party possible money transfer network locations where he/she can pay for the healthcare prescription order, and/or instructions on how to make a payment online through the money transfer network.

In an embodiment, method 200 may include sending a message to the patient and/or third party about the processing status of the healthcare prescription order (e.g., a payment of the healthcare prescription order has been received, the healthcare prescription order has been received by a designated pharmacy, the order is being processed by the pharmacy, the order has been dispatched/deliver, and/or the order is ready for pick up). The notification regarding the status of the healthcare prescription order may be sent to the patient and/or third party with or without an inquiry from the patient/third party.

In an embodiment, the third party may be located in a different place from the patient. For example, the third party may be located in different part of a city, a different city, or a different country from the patient. In an embodiment, the payment for the healthcare prescription order may be made in a currency that is different from the currency used by the pharmacy. In such cases, method 200 may further include converting the payment in a foreign currency to an amount in a local currency of the pharmacy where it is located (e.g., from US dollar to Japanese Yen, or vice versa).

In an embodiment, the healthcare prescription order in method 200 may be associated with an unique identifier. The unique identifier may be used by method 200 to process the healthcare prescription order, receive a payment of the healthcare prescription order, create a status of the healthcare prescription order, make a notification to the patient/third party, or a designated pharmacy. The unique identifier may also be used by the patient and/or a third party to make a payment for and/or and inquiry about the status of the healthcare prescription order. The unique identifier may also be used by the pharmacy to process, deliver, or make a notification about the healthcare prescription order.

Figure 3:
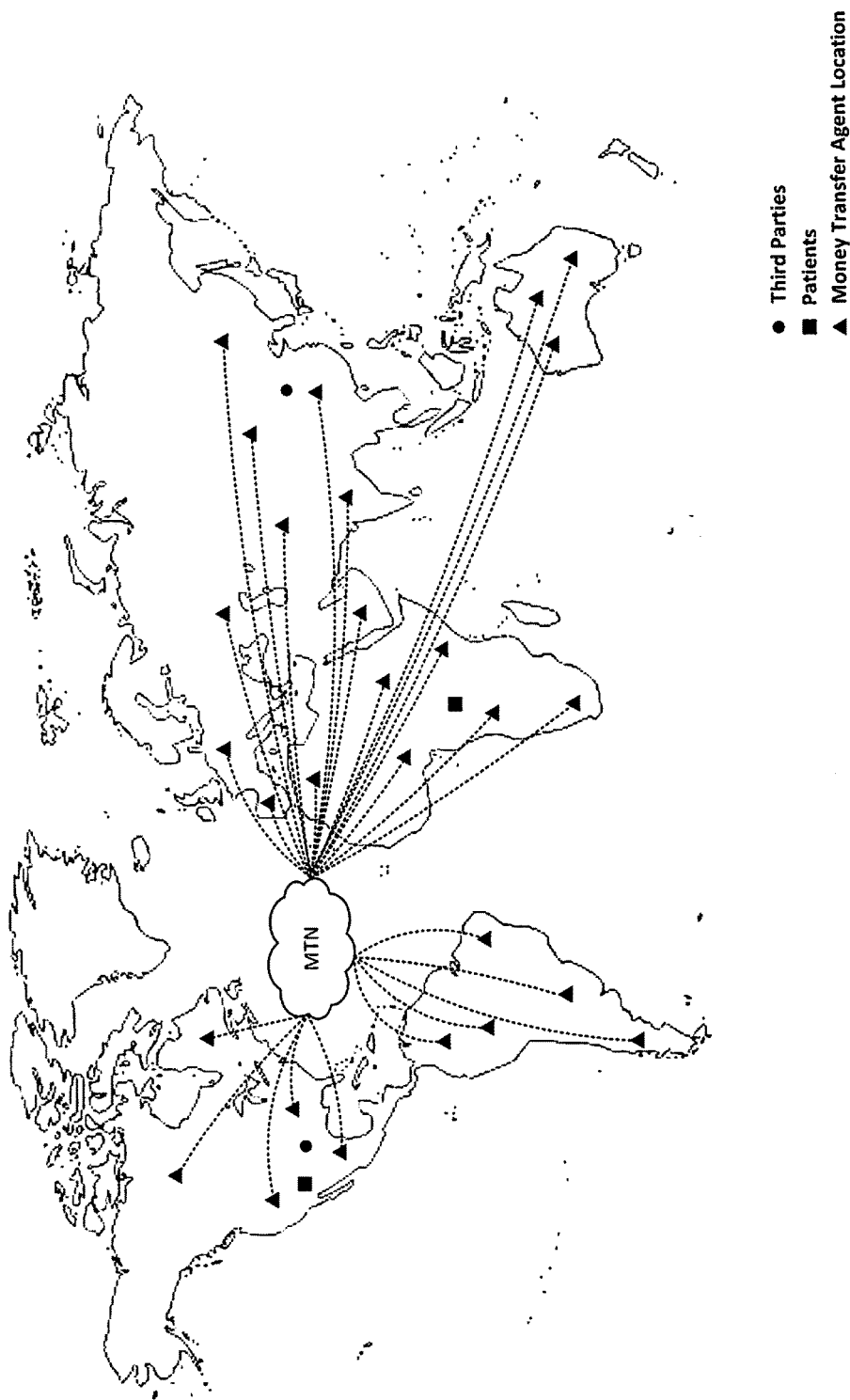
FIG. 3 is a diagram illustrating exemplary aspects for providing healthcare prescription deliver using a money transfer network in accordance with aspects of the present disclosure.

The healthcare prescription delivery method and system described above may promote health, assist travelers and/or indigent individuals to obtain healthcare, and/or fulfill another beneficial need to members of society. For example, referring to FIG. 3, a diagram illustrating exemplary aspects of healthcare delivery according to embodiments is shown. As shown in FIG. 3, a money transfer service provider may provide a money transfer network (labeled MTN in FIG. 3) that interconnects a plurality of money transfer agent locations (shown as triangles in FIG. 3), and the plurality of money transfer agent locations may be distributed across various countries. The money transfer network may include a central server (e.g., the central server 110 of FIG. 1). Additionally, each money transfer agent location operating in the money transfer may include one or more agent devices (e.g., the agent device 130 of FIG. 1). Further, the money transfer network may include kiosks (e.g., the kiosk 150 of FIG. 1). The money transfer network devices (e.g., the central server, the agent devices, and the kiosks) may be configured to facilitate processing of healthcare prescription delivery as described above with respect to FIGS. 1 and 2.

During operation according to the embodiments illustrated in FIG. 3, a patient (shown as a square in FIG. 3) in Sub Saharan Africa may not be able to pay for his/her prescription order to treat his/her life threatening disease. According to embodiments, after receiving a notification that a prescription order has been placed, the patient may initiate a request for a third party (shown as a circle in FIG. 3) to pay for his/her prescription using the patient/user device 184 (e.g., the patient may go online and make the request through a social network or other platforms), and a third party with good will can pay for the patient's prescription order through the third party device 186 using the money transfer network. The designated pharmacy can then, after receiving the payment from the money transfer network, process the prescription and deliver to the patient or notify the patient to pick it up. As another example, a Chinese student who travels to the United States for school may be in need of medical care. She saw a doctor and receives her prescription but she may have financial difficulties to pay for her prescription. The student may need her parents or relatives back in China to make the payment for the prescription so that she can receive the necessary medical care. Using the healthcare prescription delivery system 100 and method 200 described herein, the student's parents, relatives, and/or friends from a different location can go online or visit a local kiosk or money transfer agent location of the money transfer network, and use one or more graphical user interfaces (GUIs) presented by their personal computer or the kiosk, or a money transfer agent may input the information into an agent device, to provide make a payment for the student's prescription order, and the prescription will be delivered from a pharmacy directly to the student in the United States.

Further, making it possible for a patient to receive his/her prescription without traveling could generate a huge benefit to society. Traditional healthcare systems and services require a patient to physically see a doctor, obtain a prescription, and then physically travel to a pharmacy to fill the prescription. This may require a large amount of travel, time, and cost for the patient or his/her designated third party. This process may also cause further difficulties for a patient to receive the prescribed drugs when his/her illness prevents him/her from traveling for obtaining and filling the prescription. With the healthcare prescription delivery system and method disclosed herein, a patient may be able to receive medical care without leaving his/her home and from virtually anywhere. For example, an online doctor may be able to diagnose a patient based on symptoms described by the patient and prepare a prescription order for the patient. The patient or a third party pays for the healthcare prescription order, and a pharmacy fills the prescription after receiving the healthcare prescription order and a payment for it. The prescription is then delivered to the patient by the pharmacy or a third party courier service. For the patient to receive medical treatment through this system, the patient does not need to travel at all.

Although the embodiments of the present disclosure and their advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for healthcare prescription delivery comprising:
    receiving information associated with a healthcare prescription order for a patient, wherein the information is provided to a device at an agent location of a money transfer network operated by a money transfer service provider;
    validating the healthcare prescription order, wherein the validating includes:
        establishing a communication connection between a central server of the money transfer network and a server associated with a pharmacy service;
        providing at least a portion of the received information associated with the healthcare prescription order to the server;
        receiving, at the central server, a validation determination from the server of the pharmacy service, wherein the validation determination indicates whether the healthcare prescription order is valid; and
        transmitting the validation determination to the device at the agent location; and
    in response to receiving validation information that indicates the healthcare prescription order is valid:
        configuring a money transfer transaction between a receiving party and a sending party, wherein the sending party is a third party to the patient, wherein the third party is located at a different location from the patient, and wherein the receiving party is associated with the pharmacy service that validated the healthcare prescription order;
        receiving payment information associated with a payment for the healthcare prescription order, wherein the payment is provided by the third party at the agent location, wherein the payment comprises a funding amount paid in a foreign currency, and wherein the money transfer transaction is funded using the funding amount;
        initiating the money transfer transaction to provide payment for the healthcare prescription order, wherein initiating the money transfer transaction includes:
            charging the funding amount to a financial account of the sending party based on the payment information, and wherein the funding amount includes a send amount corresponding to the payment provided to the receiving party and a fee amount corresponding to a fee charged by the money transfer service provider for facilitating the money transfer transaction;
            converting the funding amount from an amount in the foreign currency to an amount in a local currency of a geographic area where the pharmacy is located;
            determining whether the amount converts evenly into the amount in the local currency; and
            in response to a determination that the amount in the foreign currency does not convert evenly into the amount in the local currency, reducing the fee such that the amount in the foreign currency converts evenly into the amount in the local currency; and
        transmitting a notification to the pharmacy service that the payment has been received from the sending party.

2. The method of claim 1, further comprising storing a record associated with the money transfer transaction at a database, wherein the record includes the information associated with the healthcare prescription order, the payment information, and money transfer transaction information associated with the money transfer transaction.

3. The method of claim 1, further comprising sending, by the device, a message confirming a dispatching of the prescription to the patient or the third party.

4. The method of claim 1, wherein the payment for the healthcare prescription order is paid online or in person using resources of the money transfer network.

5. The method of claim 1, wherein the healthcare prescription order is associated with a unique identifier.

6. The method of claim 5, further comprising sending a message indicating a status of the healthcare prescription order to the patient or third party in response to an inquiry using the unique identifier.

7. The method of claim 5, wherein the payment for the healthcare prescription order is provided using the unique identifier.

8. A money transfer network device for healthcare prescription delivery comprising:
    at least one processor configured to:
        receive information associated with a healthcare prescription order for a patient, wherein the information is provided to a device at an agent location of a money transfer network operated by a money transfer service provider;
        validate the healthcare prescription order, wherein the validating includes:
            establish a communication connection between a central server of the money transfer network and a server associated with a pharmacy service;
            provide at least a portion of the received information associated with the healthcare prescription order to the server;
            receive, at the central server, a validation determination from the server of the pharmacy service, wherein the validation determination indicates whether the healthcare prescription order is valid; and
            transmit the validation determination to device at the agent location;
        in response to receiving validation information that indicates the healthcare prescription order is valid:
            configure a money transfer transaction between a receiving party and a sending party, wherein the sending party is a third party to the patient, wherein the third party is located at a different location from the patient, and wherein the receiving party is associated with the pharmacy service that validated the healthcare prescription order;
            receive payment information associated with a payment for the healthcare prescription order, wherein the payment is provided by the third party at the agent location, wherein the payment comprises a funding amount paid in a foreign currency, and wherein the money transfer transaction is funded using the funding amount;

initiate the money transfer transaction to provide payment for the healthcare prescription order, wherein initiating the money transfer transaction includes:
  charging the funding amount to a financial account of the sending party based on the payment information, and wherein the funding amount includes a send amount corresponding to the payment provided to the receiving party and a fee amount corresponding to a fee charged by the money transfer service provider for facilitating the money transfer transaction;
  converting the funding amount from an amount in the foreign currency to an amount in a local currency of a geographic area where the pharmacy is located;
  determining whether the amount converts evenly into the amount in the local currency; and
  in response to a determination that the amount in the foreign currency does not convert evenly into the amount in the local currency, reducing the fee such that the amount in the foreign currency converts evenly into the amount in the local currency; and
  transmit a notification to the pharmacy service that payment has been received by the sending party; and
a memory communicatively coupled to the at least one processor.

9. The device of claim 8, wherein the at least one processor is further configured to store a record associated with the money transfer transaction at a database, wherein the record includes the information associated with the healthcare prescription order, the payment information, and money transfer transaction information associated with the money transfer transaction.

10. The device of claim 8, wherein the at least one processor is further configured to send a message confirming a dispatching of the prescription to the patient or the third party.

11. The device of claim 8, wherein the payment for the healthcare prescription order is paid online or in person using resources of the money transfer network.

12. The device of claim 8, wherein the healthcare prescription order is associated with a unique identifier.

13. The device of claim 12, wherein the at least one processor is further configured to send a message indicating a status of the healthcare prescription order to the patient or third party in response to an inquiry using the unique identifier.

14. The device of claim 12, wherein the payment for the healthcare prescription order is provided based on the unique identifier.

15. A non-transitory computer-readable storage medium storing instructions that, when executed by a processor, cause the processor to perform operations comprising:
receiving information associated with a healthcare prescription order for a patient, wherein the information is provided to a device at an agent location of a money transfer network operated by a money transfer service provider;
validating the healthcare prescription order, wherein the validating includes:
  establishing a communication connection between a central server of the money transfer network and a server associated with a pharmacy service;
  providing at least a portion of the received information associated with the healthcare prescription order to the server;
  receiving, at the central server, a validation determination from the server of the pharmacy service, wherein the validation determination indicates whether the healthcare prescription order is valid; and
  transmitting the validation determination to device at the agent location; and
in response to receiving validation information that indicates the healthcare prescription order is valid:
  configuring a money transfer transaction between a receiving party and a sending party, wherein the sending party is a third party to the patient, wherein the third party is located at a different location from the patient, and wherein the receiving party is associated with the pharmacy service that validated the healthcare prescription order;
  receiving payment information associated with a payment for the healthcare prescription order, wherein the payment is provided by the third party at the agent location, wherein the payment comprises a funding amount paid in a foreign currency, and wherein the money transfer transaction is funded using the funding amount;
  initiating the money transfer transaction to provide payment for the healthcare prescription order, wherein initiating the money transfer transaction includes:
    charging the funding amount to a financial account of the sending party based on the payment information, and wherein the funding amount includes a send amount corresponding to the payment provided to the receiving party and a fee amount corresponding to a fee charged by the money transfer service provider for facilitating the money transfer transaction;
    converting the funding amount from an amount in the foreign currency to an amount in a local currency of a geographic area where the pharmacy is located;
    determining whether the amount converts evenly into the amount in the local currency; and
    in response to a determination that the amount in the foreign currency does not convert evenly into the amount in the local currency, reducing the fee such that the amount in the foreign currency converts evenly into the amount in the local currency; and
  transmitting a notification to the pharmacy service that payment has been received by the sending party.

* * * * *